(12) United States Patent
Igwebuike et al.

(10) Patent No.: US 11,452,639 B2
(45) Date of Patent: Sep. 27, 2022

(54) WOUND CARE DEVICE FOR DEBRIDING WOUNDS

(71) Applicant: Coloplast A/S, Humlebaek (DK)

(72) Inventors: Henning Igwebuike, Lynge (DK); Kent Hoeier Nielsen, Oelstykke (DK)

(73) Assignee: Coloplast A/S, Humlebaek (DK)

( * ) Notice: Subject to any disclaimer, the term of this patent is extended or adjusted under 35 U.S.C. 154(b) by 62 days.

(21) Appl. No.: 16/648,675

(22) PCT Filed: Sep. 18, 2018

(86) PCT No.: PCT/DK2018/050229
§ 371 (c)(1),
(2) Date: Mar. 19, 2020

(87) PCT Pub. No.: WO2019/057256
PCT Pub. Date: Mar. 28, 2019

(65) Prior Publication Data
US 2020/0214896 A1 Jul. 9, 2020

(30) Foreign Application Priority Data

Sep. 20, 2017 (DK) .......................... PA 2017 70707

(51) Int. Cl.
*A61F 13/00* (2006.01)
*A61B 17/32* (2006.01)

(52) U.S. Cl.
CPC ........ *A61F 13/00029* (2013.01); *A61B 17/32* (2013.01); *A61F 13/00042* (2013.01);
(Continued)

(58) Field of Classification Search
CPC .......... A61F 13/00029; A61F 13/00042; A61F 13/00; A61F 13/00068; A61F 13/00017;
(Continued)

(56) References Cited

U.S. PATENT DOCUMENTS 3,707,012 A 12/1972 Lane
4,055,029 A 10/1977 Kalbow
(Continued)

FOREIGN PATENT DOCUMENTS

DE 102014106518 A1 * 11/2015 ....... A61F 13/00008
EP 0552933 A1 7/1993
(Continued)

OTHER PUBLICATIONS

Martin Deibler, Foam wound dressing for negative pressure therapy, Nov. 12, 2015 (Year: 2015).*
(Continued)

*Primary Examiner* — Tatyana Zalukaeva
*Assistant Examiner* — Nhu Q. Tran
(74) *Attorney, Agent, or Firm* — Coloplast Corp., Coloplast A/S; Nick Baumann

(57) ABSTRACT

A wound care device for debriding a wound, said device is in the form of a foam pad with two layers of different foams. At one surface of the device is provided a pattern of grooved at the central portion. The grooves improve the ability of removing and collecting debris from a wound during cleaning of such.

16 Claims, 6 Drawing Sheets

(52) U.S. Cl.
CPC ............. *A61B 2017/320004* (2013.01); *A61B 2017/320008* (2013.01)

(58) Field of Classification Search
CPC .......... A61F 13/0216; A61F 13/00004; A61M 1/0088; A61M 1/90; A61M 2205/04; A61B 17/3205; A61B 17/32; A47L 13/16
See application file for complete search history.

(56) References Cited

U.S. PATENT DOCUMENTS

| | | | |
|---|---|---|---|
| 4,111,666 | A | 9/1978 | Kalbow |
| 6,574,825 | B1 | 6/2003 | Boldy |
| 2004/0092895 | A1 | 5/2004 | Harmon |
| 2006/0135050 | A1* | 6/2006 | Petersen ................. B24D 15/04 451/523 |
| 2010/0125233 | A1* | 5/2010 | Edward S. ........ A61F 13/00068 602/42 |
| 2011/0270206 | A1* | 11/2011 | Jensen .............. A61F 13/00995 604/369 |
| 2016/0022885 | A1* | 1/2016 | Dunn ..................... A61M 1/90 604/319 |
| 2017/0203406 | A1* | 7/2017 | Ganapathiappan ..... B24B 37/26 |
| 2018/0272052 | A1* | 9/2018 | Locke ................... A61M 1/743 |
| 2018/0353336 | A1* | 12/2018 | Locke ............... A61F 13/15203 |

FOREIGN PATENT DOCUMENTS

| | | |
|---|---|---|
| EP | 1310226 A2 | 5/2003 |
| EP | 2985013 A2 | 2/2016 |
| GB | 2429157 A | 2/2007 |
| GB | 2480503 A | 11/2011 |
| JP | 2000014591 A | 1/2000 |
| JP | 2000041928 A | 2/2000 |
| JP | 2004275687 A | 10/2004 |
| JP | 2005199001 A | 7/2005 |
| WO | 9826657 A1 | 6/1998 |
| WO | 2015169637 A1 | 11/2015 |
| WO | 2017019868 A1 | 2/2017 |

OTHER PUBLICATIONS

Meads Catherine et al., "The Debrisoft? Monofilament Debridement Pad for Use in Acute or Chronic Wounds: A Nice Medical Technology Guidance", Applied Health Economics and Health Policy, vol. 13, No. 6, Dec. 1, 2015, ISSN: 1175-5652.

* cited by examiner

WOUND CARE DEVICE FOR DEBRIDING WOUNDS

The invention relates to a wound care device for debriding and cleaning wounds and a method of debriding and cleaning wounds.

SUMMARY OF THE INVENTION

The present disclosure provides aspects of wound care device according to the appended claims. The disclosure further provides a method of cleaning a wound as disclosed herein.

BRIEF DESCRIPTION OF THE DRAWING

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
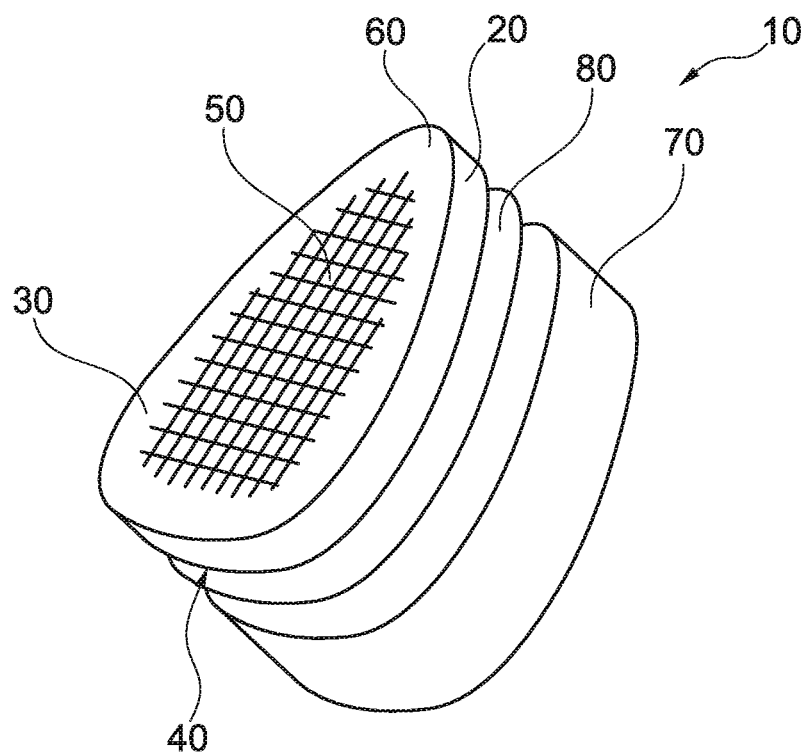
FIG. 1 illustrates an isometric, exploded view of an embodiment.

Embodiments, and features of the various exemplary embodiments described in this application, may be combined with each other ("mixed and matched"), unless specifically noted otherwise.

In the following Detailed Description, reference is made to the accompanying drawings, which form a part hereof, and in which is shown by way of illustration specific embodiments in which the invention may be practiced. Because components of embodiments can be positioned in different orientations, the directional terminology is used for purposes of illustration and is in no way limiting. It is to be understood that other embodiments may be utilized, and structural or logical changes may be made without departing from the scope of the present invention. The following detailed description, therefore, is not to be taken in a limiting sense, and the scope of the present invention is defined by the appended claims.

The longitudinal direction herein describes the direction of a longitudinal axis extending from a distal end to a proximal end of the wound care device. The transverse or radial direction is the direction perpendicular to the longitudinal direction, which corresponds to the direction across the device.

The use of the phrase "substantially" as a qualifier of certain features or effects throughout this disclosure, is intended to simply mean that any deviations are within tolerances that would normally be expected by the skilled person in the relevant field.

Herein, the phrases "debris" and "slough" both address the greasy material that may be formed on the surface of a wound. Such debris may be home for bacterial growth as well as it may obstruct wound healing and is therefore desired to remove the debris and slough during cleaning of the wound.

Embodiments relate to a wound care device for debriding a wound, said device comprising a first foam layer having a first and a second surface, the first surface comprising a central portion and an edge portion, where the central portion is provided with a plurality of grooves and ridges (with the grooves being for accepting debris from the wound), and the edge portion is continuous (grooves and ridges absent) and the second surface of the first foam layer is provided with a second foam layer.

The wound care device may be in the form of a foam pad for cleansing and debriding of wounds. The device comprises two different foam layers, such as a coarse foam and a soft foam, to provide optimal handling as well as multi-functionality.

Using a foam pad for cleaning and debriding of a wound provides an advantage that the foam pad distributes pressure over the wound more evenly compared to a cloth or tissue. Wound, especially chronic wound may be fragile and may be susceptible to be damaged if exposed to unnecessary pressure.

In embodiments, the first and the second foam layers are joined to each other by an adhesive, for example a hot-melt adhesive. In embodiments, the foam layers are joined to each other by welding or lamination.

In embodiments, at least one further layer is inserted between the first and the second foam layer. In one implementation, such layer is a reinforcing layer, providing more rigidity to the device.

In embodiments, the first and the second foam layers are joined to each other by a layer of double-sided adhesive tape.

In embodiments, the wound care device consists of a first foam layer and a second foam layer and a connecting layer, the first foam layer having a first surface and a second surface and the second surface of the first foam layer being joined to the second foam layer. The first and the second foam layers are joined to each other by a connecting layer 80 (FIG. 1) such as an adhesive layer, double-sided adhesive tape or they may be joined by lamination.

The central portion of the first surface of the first foam layer is provided with grooves and ridges. The ridges are zones of the first foam layer without grooves, and the grooves are defined by side walls of the ridges. The ridges are zones of the first foam layer having a thickness corresponding to the overall thickness of the foam layer whereas the grooves have a smaller thickness than the overall thickness of the first foam layer, the grooves being slits cut in the first foam layer. The grooves are configured to accepting debris from the wound. In embodiments, the grooves are in the form of grooves extending substantially perpendicular to the first surface of the first foam layer.

In embodiments, the side walls of the ridges have angular edges. The angular edges of the side walls help to assist in scraping off or otherwise obtaining the debris from the wound and directing the debris into the grooves. In embodiments, the grooves are only cut partly through the first foam layer, leaving an uninterrupted part of the first foam layer at a bottom of the grooves, next to the second surface of the first foam layer. In other words, in embodiments the grooves have a depth such that they extend partway, but not entirely, through a thickness of the first foam layer.

In embodiments, the grooves may be cut through the entire first foam layer, or even through a part of the second foam layer.

In embodiments, the grooves may be cut with a cutting apparatus or by laser. Cutting with a cutting apparatus, the grooves can be very narrow, whereas cutting by laser can create broader grooves as foam material is removed by burning during the process.

The grooves facilitate collection of sloughy material such as debris from a wound to the device. If a distance between any two grooves is too small, the ridges could potentially collapse under pressure or even break. On the other hand, if the distance between any two grooves is too high, the grooves could lose the ability to collect slough.

In embodiments, the grooves extend at least 50%, such as 60%, such as 70%, such as 80% or even 90% of the thickness of the first foam layer. In embodiments, the grooves have a depth of up to 100% of the thickness of the first foam layer. In embodiments, the grooves may extend through the entire first foam layer and into the second foam layer. In embodiments, the grooves have a depth of 5-12 mm, such as 6-10 mm, such as 6-9 mm, such as 7-8 mm. The depth of the grooves can be determined as the distance from the surface of the first layer to the bottom of the groove, the distance being perpendicular to the first surface of the first foam layer. The thickness of the first foam layer can be determined as the distance from the first surface to the second surface, measured perpendicular to the first surface. In embodiments, the first foam layer has a uniform thickness over the entire layer.

In embodiments, the grooves are arranged in a pattern. In embodiments, the grooves are arranged in a pattern of parallel lines. In embodiments, the grooves are arranged in a pattern of a first set of parallel lines crossed by a second set of parallel lines, optionally being oriented perpendicular to the first set of lines, defining a pattern of square-shaped ridges between the grooves, a mesh like pattern. In embodiments, a first set of grooves extend in one direction and another set of grooves extend in a direction different to the direction of the first set of grooves.

The ridges are defined as the portion between the grooves. In embodiments, the ridges have shapes being square, rectangular, triangular or other geometric shapes defined by lines or curves. In embodiments, the distance between the grooves, herein called the mesh size, is 3-12 mm, such as 4-10 mm, such as 3-9 mm, such as 4-8 mm, or even 5-7 mm.

When cleaning or debriding a wound, the device can advantageously be moved in circular movements by a person, such as a health care professional, holding the wound care device in one hand, while applying a light pressure to the wound and the grooves will collect the debris from the wound. Providing the wound care device with grooves increases the cleaning surface capacity of the significantly.

The grooves increase the ability of the device to collect debris and slough from the wound. Furthermore, by providing the first foam layer with the grooves, it is possible to use a softer foam for the debridement of the wound, and a softer foam is more gentle to the wound.

In embodiments, the continuous/uninterrupted edge portion of the first surface has a width of 2-20 mm, such as 3-15 mm, such as 4-12 mm or even 5-10 mm. In one embodiment, the width of the continuous/uninterrupted edge portion is approximately 10 mm. In embodiments, the width of the continuous/uninterrupted edge portion is at least the same as the distance between two neighbouring grooves. The width of the continuous/uninterrupted edge portion is measured as the distance from an outer periphery of the first surface of the first foam layer to an outer periphery of the central portion, where the pattern of grooves end.

The edge portion of the first surface is in the form of a continuous/uninterrupted zone. The edge of the foam pad may be exposed to more stress than the central portion during use, which could lead to foam breakage. Creating a continuous zone without grooves at the edge portion, surrounding the central portion having grooves, a more robust edge is created, because stress is distributed to a larger foam area.

The shape of the wound care device facilitates several purposes including among others good ergonomic handling such as the ability to use entire surface of the device while working with it. The shape of the device produces an intuitive understanding of how to orient/use the device.

In embodiments, the device has a first outer external surface—being the first surface of the first foam layer, and a second outer external surface—being the surface of the second foam layer facing away from the first foam layer. The edge of the first and the second outer external surface are connected by a side portion circumferencing the device. In embodiments, the side portion is substantially perpendicular to the first surface.

An outline of the wound care device, defined as the outer periphery of the first foam layer, can have any suitable shape. In embodiments, the shape is round, oval triangular, square, droplet-shape or other geometric or non-geometric shapes. In embodiments, the outline is defined by corners and substantially straight lines connecting the corners. In embodiments, the corners of the device are rounded. In embodiments, one or more of the corners of the device is/are more angular to facilitate cleaning narrow spaces in the wound. In embodiments, the shape may be ergonomic to provide a good hand-grip.

By substantially straight lines is here meant that a length of the curve defining the line between two corners is only slightly longer (less than 15%, or more preferred less than 10%, such as less than 5%) than the chord between the same two corners. In other words, a surface area of one side of the device is less than 15% (such as less than 10% or less than 5%) larger than an area of the plane spanned by the two corners of the side.

In embodiments, the device has rounded corners. By rounded corners is meant that the transition from one surface to another around a circumferential cross-section of the device follows a rounded curve.

Another way of describing this is that the outline of the device consists of a first three pieces having a first small curvature (large radius) joined alternately with a second three pieces having a second larger curvature (small radius).

In embodiments, the outline/shape of the wound care device is symmetrical around a central longitudinal axis. In embodiments, the device is longer in the axial direction than in the radial direction (being the direction perpendicular to the axial direction. In embodiments, the device is 5% longer in the axial direction, such as 10%, such as 15%, such as 20%, such as 25% or even 30% longer in the axial direction.

In embodiments, the device is 20-25% longer in the axial direction than in the radial direction.

In embodiments, the outline/shape of the wound care device has a substantially triangular outline.

Both foam layers need to be of a type having tensile strength that is sufficient to avoid breaking of the foam when in contact with the wound and configured to avoid shedding foam particles into the wound during usage.

In embodiments, the first foam layer is a soft foam. In embodiments, softness can be defined by the perception of a polyester foam with a PPI (Pore per Inch) of 70 to 90, and a CLD (Compression Load Deflection) of @25%=0.30 to 0.40 psi/CLD@65%=0.50 to 0.60 psi. In embodiments, the foam may appear soft and gentle to the patient as well as it is flexible enough to facilitate the grooves to collect debris when rubbed over a wound, while also having a tensile strength sufficient to avoid breaking when in contact with the wound and avoid shedding foam particles into the wound during usage.

In embodiments, the first foam layer comprises a hydrophilic foam. In embodiments, the first foam layer comprises a polyurethane foam such as a polyester polyurethane foam.

The first foam layer is intended for use on the wound bed and should maintain a level of softness that reduces the risk of pain during use as well as reducing the risk of damage to granulation tissue. In embodiments, the soft foam is able to absorb fluid and release it again under pressure, thereby donating moisture to the wound bed and support cleaning of it. In embodiments, the first foam layer is able to absorb/incorporate viscous material such as slough and debris into its structure.

In embodiments, the second foam layer is coarser than the first foam layer. The second foam layer serves at least two primary functions, it works as a grip for handling the device and it can be used on the wound bed and surrounding skin to remove skin scales and loosening debris/devitalised tissue in the wound bed.

In some implementations, the wound care device is used with the second foam layer facing the wound for initial cleaning and then turned around to make the first foam layer face the wound for further cleaning.

In embodiments, the second foam layer comprises a certain level of coarseness in order to function effectively while not becoming so coarse that there is a risk of injury to the wound. In embodiments, the second foam layer has a coarseness level higher than the first foam layer. In embodiments, coarseness can be defined by the perception of a polyester foam with a PPI of 40-50, and a CLD of @25%=0.40 to 0.50 psi/CLD@65%=0.65 to 0.75 psi.

In embodiments, the second foam layer is non-absorbing. In embodiments, the second foam layer is hydrophobic.

In embodiments, the first foam layer has a thickness less than the thickness of the second foam layer. In embodiments, the ratio between the thickness of the first and the second foam layer is 1:3, such as 1:2.5 and even such as 1:2. In embodiments the ratio between the thickness of the first and the second foam layer is between 1:1 and 1:3, such as between 1:1.5 and 1:2.5. In embodiments the ratio between the thickness of the first and the second foam layer is 1:2.

In embodiments, the first foam layer and the second foam layer have equal thickness.

In embodiments, the first foam layer is thicker than the second foam layer. In embodiments, the ratio between the thickness of the second and the first foam layer is 1:3, such as 1:2.5 and even such as 1:2.

In embodiments, the total thickness of the wound care device is between 25 mm and 40 mm, such as between 28 mm and 35 mm, or even between 30 mm and 33 mm.

In embodiments, the second foam layer has a substantially uniform thickness. In embodiments, the thickness of the second foam layer is between 10 mm and 30 mm, such as between 15 mm and 25 mm, such as between 18 mm and 23 mm.

In embodiments, the first foam layer has a substantially uniform thickness, apart from the grooves. In embodiments, the thickness of the first foam layer is between 5 mm and 15 mm, such as between 8 mm and 13 mm, such as between 9 mm and 11 mm.

In embodiments, the first foam layer is 10 mm thick. It has been found that the thickness of the first foam layer should strike a balance between slough incorporation capability and handling performance when wetted. In embodiments, the thickness of approximately 10 mm of the first foam layer has been found to provide a good balance between handling, slough incorporation and ability to wet the wound bed being cleaned.

In embodiments, the second foam layer is 22 mm thick. The coarse structure of the second foam layer facilitates the second foam layer to retain its structure and stiffness even when wetted and serves as the primary layer for the user to hold on to when handling the product. In embodiments, a thickness of 22 mm provides good ergonomic handling.

In embodiments, the wound care device comprises one or more of antibacterial agents, cleaning agents, healing promoting compounds and/or skin soothing substances.

Embodiments further relate to a method of cleaning a wound, comprising the steps of providing a wound care device for debriding a wound, said device comprising a first foam layer having a first and a second surface, the first surface comprising a central portion and an edge portion, where the central portion is provided with a plurality of grooves and ridges, and the edge portion is continuous and the second surface of the first foam layer is provided with a second foam layer, bringing the first layer in contact with the wound, performing a rotating movement while applying a light pressure to remove slough and debris from the wound.

In embodiments, method further comprises the step of wetting the wound care before contacting the wound.

In embodiments, the method further comprises initially bringing the second foam layer in contact with the wound and using the second foam layer to remove rough debris.

In embodiments, the wound care device is contained in a package. In embodiments, the device may be provided in sterile packaging. In embodiments, the wound care device is stored in dry state. In embodiments, the device is stored in wetted state in the package.

In the following detailed description, reference is made to the accompanying drawings. The drawings form a part of this specification and illustrate exemplary embodiments for practicing the invention. It is to be understood that other embodiments may be utilized, and structural or logical changes may be made without departing from the scope of the invention. The detailed description describes examples for practicing the invention and is not to be read to limit the scope of the invention. The scope of the invention is defined by the attached claims.

Figure 2:
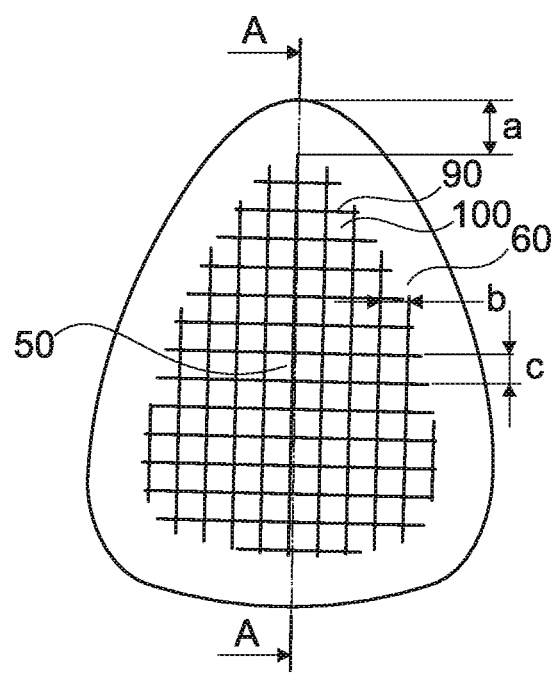
FIG. 2 illustrates an embodiment seen from a first surface of a first foam layer of the device.

FIG. 1 is an isometric and exploded view of an embodiment of the wound care device 10. The wound care device 10 comprises a first foam layer 20 having a first surface 30 and a second surface 40 opposite the first surface. The first surface 30 comprises a central portion 50 and an edge portion 60 circumferencing the central portion 50. The central portion 50 is provided with a pattern of grooves and ridges. On the second surface 40 of the first foam layer 20, a second foam layer 70 is attached. The second foam layer 70 is shown to be thicker than the first foam layer 20. The outline (shape) of the device 10 is substantially triangular with rounded corners. The device 10 of the illustrated embodiment is symmetric along a central longitudinal axis (FIG. 2). The triangular shape is ergonomic and pleasant to hold in the hand and work with cleaning a wound.

Figure 3:
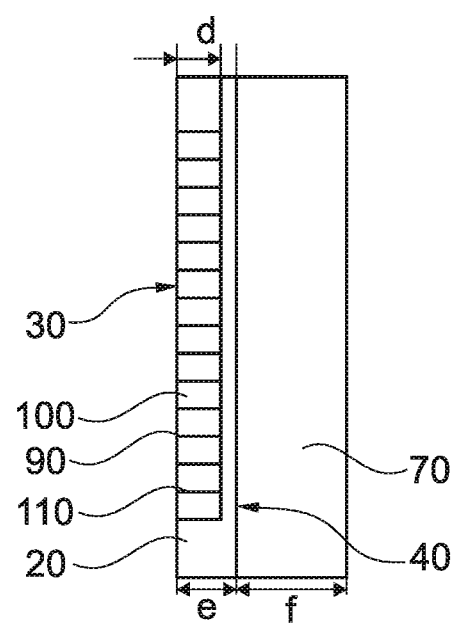
FIG. 3 illustrates a cross-section of the embodiment of FIG. 2, cut along the A-A line.

FIG. 2 shows a plan view of the first surface 30 of the device 10 and FIG. 3 shows a cross-section of the embodiment of FIG. 2, along a central axis, marked A-A in FIG. 2. The central portion 50 has a plurality of grooves 90 and ridges 100. The grooves 90 are defined by side walls 110 of the ridges 100. The grooves 90 are cut in the foam in a direction being substantially perpendicular to the first surface 30 of the first foam layer 30. In the illustrated embodiments, the side walls 110 of the ridges 100 have sharp edges. The grooves 90 are configured to collect debris from the wound. The sharp edges of the side walls 110 help to assist in scraping or otherwise obtaining the debris from the wound and getting the debris into the grooves 90. In the illustrated embodiment, the grooves 90 are arranged in a pattern of a first set of parallel lines crossed by a second set of parallel lines, optionally being perpendicular to the first set of lines, thereby defining a pattern of square-shaped ridges 100 between the grooves 90. The distance between the grooves of the first set of lines are marked in the FIG. 2 as b and the distance between the grooves of the second set of lines are marked in the FIG. 2 as c. The grooves 90 are cut partly through the first foam layer 20, leaving an uninterrupted part of the first foam layer 20 next to the second surface 40 of the first foam layer 20. The depth of the grooves is marked as d. The edge portion 60 is continuous in the sense it is not provided with grooves 90. The width of the continuous edge portion is marked in FIG. 2 as a.

EXPERIMENTAL

The following Examples show tests which quantify the ability of a device to remove a test media from a test surface when pressed and repeatedly translated in a circular motion and conducted by a robot arm. Reported results are the weight of test substance [g] debrided by test specimen. The purpose of the test is to show the effect of the foam material and the effect of applying grooves to the wound care device.

The tests have been conducted with different foam types and compared with test results from a test performed on a known debridement product (not foam-based).

Materials:

Test media (artificial wound slough): Egg slough with controlled Viscosity. Egg slough consists of freeze-dried eggs suspended in water. The viscosity of the egg-slough is adjusted by the amount of water added.

Sample A:

Polyether based polyurethane foam sample size: 100× 100×10 mm. The specifications of the foam of Sample A appears from Table 1.

Sample B:

Polyester based polyurethane foam, sample size: 100× 100×10 mm. The specifications of the foam of Sample B appears from Table 1.

Sample C:

DEBRISOFT debridement product, sample size 100× 100×10 mm, the product consists of monofilament polyester fibres, with the reverse side being coated with polyacrylate.

TABLE 1

| Property | Unit | specification | Sample B |
|---|---|---|---|
| Pore Size | Pores/cm | 20-30 | 30-33 |
| Density | Kg/m$^3$ | 24 | 28-35 |
| Tensile Strength | KPa | 125 | 206 |
| Elongation | % | 175 | 380 |
| Tear Strength | N/cm | 5.0 | 6.3 |
| CLD@25% | KPa | 2.6 | 1.37 |
| CLD@65% | KPa | Max 15 | 2.75 |
| Compression set @50% | % | — | 20 |

Testing is done with Robot Setup UR3: Universal Robots, Denmark.

Figure 4:
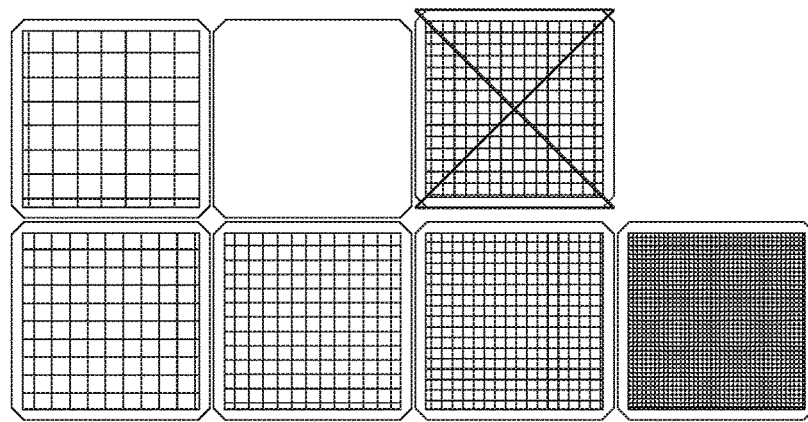
FIG. 4 schematically illustrates different embodiments of grooves of a first surface of a wound care device.

Grooves are cut with laser on a Universal Laser in "I" P55% and S90% resulting in grooves with depth of 7-8 mm. Test data rely on the following mesh design: 3 mm, 5 mm, 7 mm, 9 mm, 12 mm and a reference sample without grooves. 10 mm edge portion is free off groves. All the mesh designs can be seen in FIG. 4.

Before each test a well-defined amount of test media was added to the test surface to emulate a wound. The test then consisted of 6 test segments with measurements after each segment to provide thorough information about the debridement performance and mechanism. Reported results consist mainly of the weight of test media remaining on the test surface after each segment and the number of circular translations necessary to achieve acceptable cleaning (or if this is even possible).

One test segment consisted of compressing the sample and then performing a number of circular movements after which the sample was relieved of pressure and the remaining test media was inspected and weighed.

The less test media is left on the test surface the better the test specimen and the quicker that test media is removed, the better.

Example 1

Testing Mesh Size Versus Repetitions

In this test was used egg slough with viscosity about 48 Pa·s and foam was Sample A.

Figure 5:
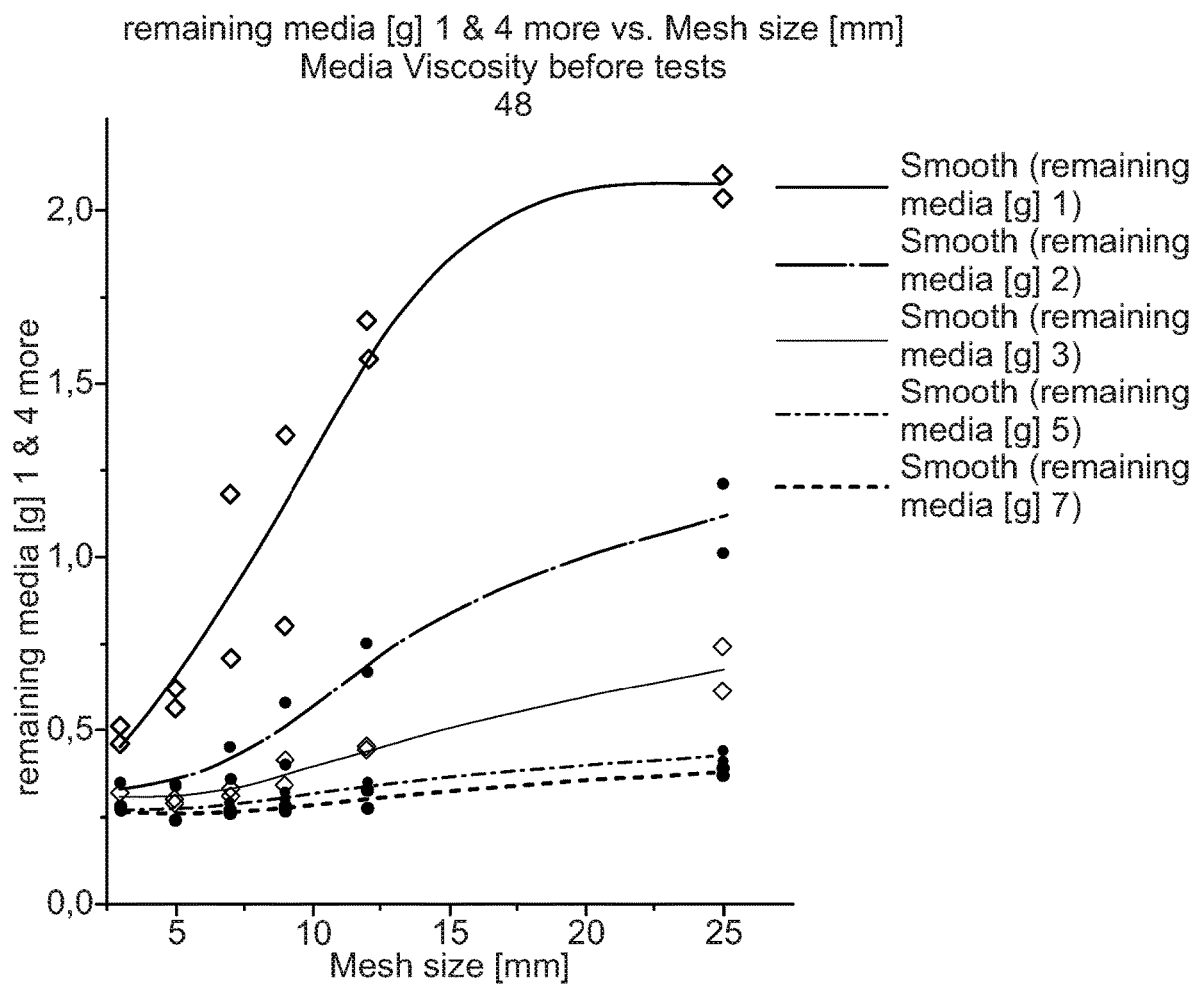
FIG. 5 illustrates the influence of mesh design.

The graphs in FIG. 5 show that after 1 test segment (which is equal to 5 circular translations of the sample on the test surface) the sample with lower mesh spacing had higher adsorption. The 3 mm mesh was best in the test series.

Example 2

Testing Effect of Varying Initial Test Media

Samples: Sample A, mesh sizes: 3, 5, 7, 9, 12 mm and a reference sample (20 mm).

Test media was used in three amounts: 5, 10, 15 g. Triple estimation.

Figure 6:
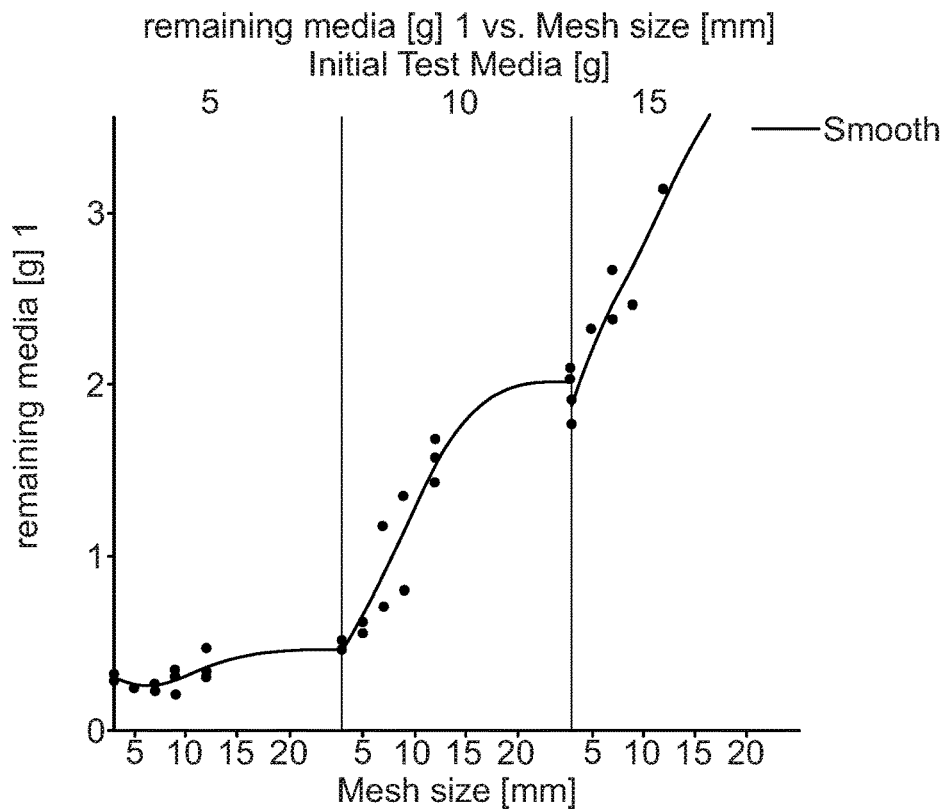
FIGS. 6 and 7 illustrate the influence of amount of test media.

Results from after the first test segment (5 circular motions) can be seen in FIG. 6. The results show the same progress with use of different initial amounts of test media; that smaller mesh size provides the best absorption/adsorption. The tested samples generally achieve the best results with the smallest initial test media size of 5 g.

Figure 7:
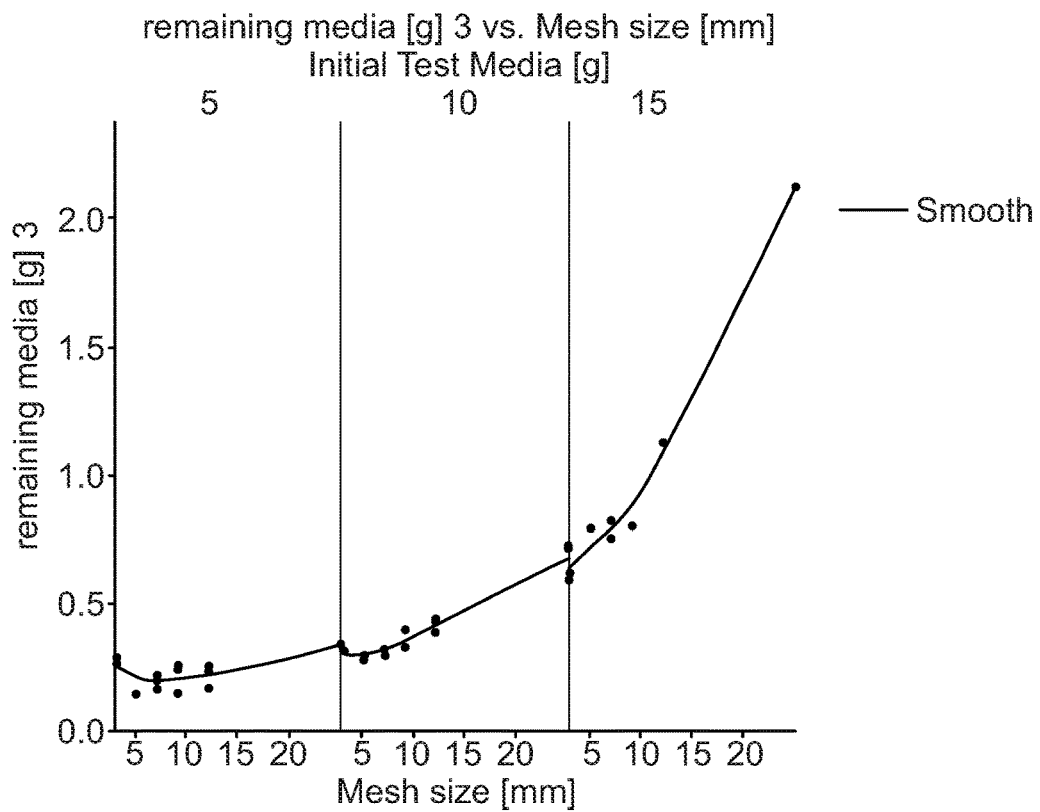

The results after 3 segments (3*5 circular movements) can be seen in FIG. 7. The results show the same progress as after the first segment, but the relative difference between groove designs was less pronounced. All tested designs continued to show the best result with a small initial test media size of 5 g. Note that the reference sample with no grooves is shown as 25 mm in the graph in FIGS. 6 and 7.

Example 3

Comparison of Different Foams and Debridement Product Samples: Sample A, B and C In FIG. 8 a one-way analysis of initial adsorption/absorption can be seen, both foam samples, Sample a and Sample B, are plain and have no grooves. The left figure shows the results after 1 segment, and it is very clear that Sample B has the best performance and Sample A the worst. The results are different if we see the results after 5 segments, here Sample B and Sample A show similar good performance while Sample C remains the worst with only a minor improvement with repeated movement.

FIG. 8: Results from comparison of performance of Sample A, B and C. All the samples testes are plain and has no mesh design. Left figure shows performance after 1 segment and right figure shows performance after 5 segments.

Figure 8A:
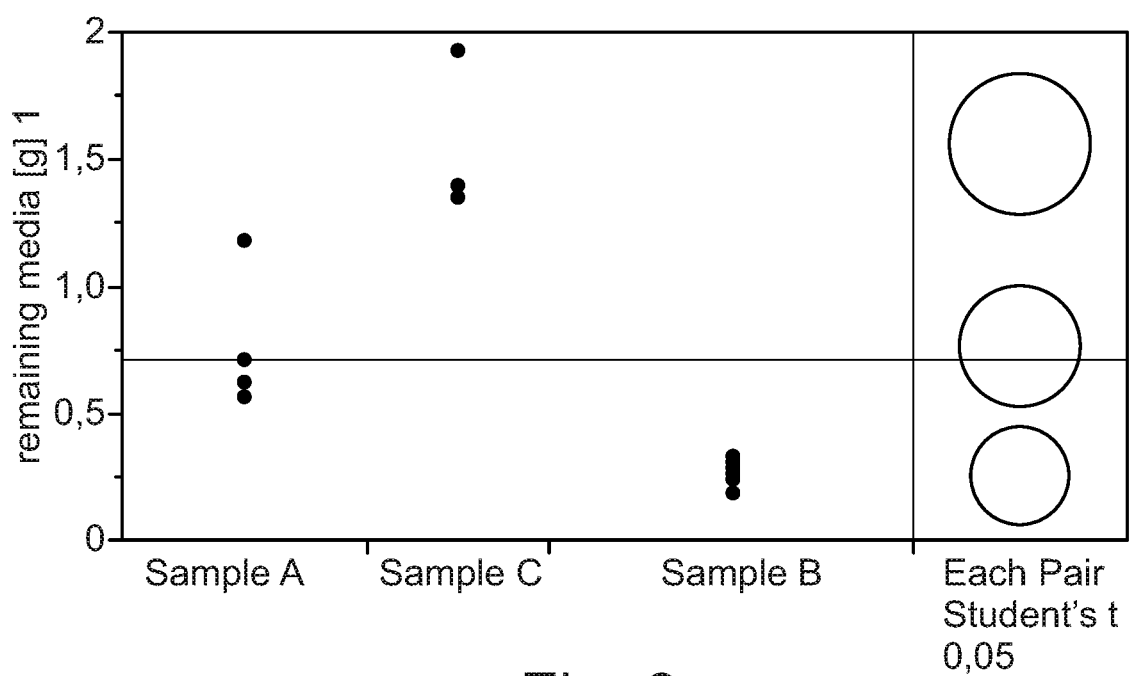
FIGS. 8a and 8b show different foams compared to a debridement product.
Figure 8B:
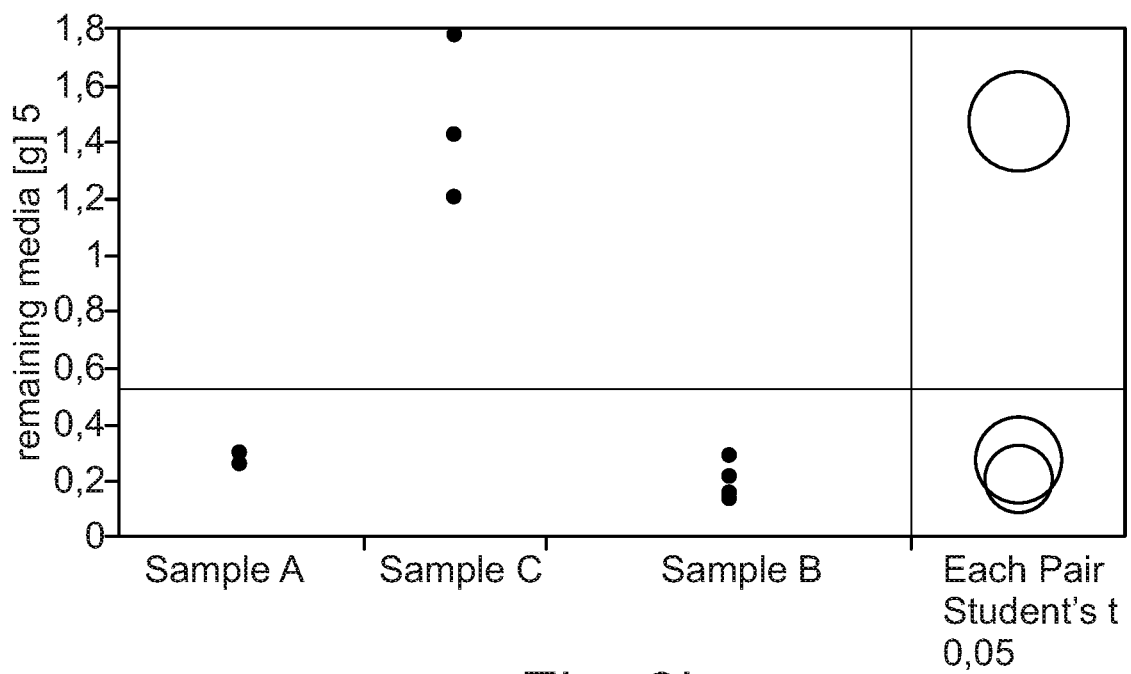

In FIGS. 8a and 8b show the result of a one-way analysis of the two foams samples, Sample A and Sample B, compared to known debridement product, Sample C. Only test samples with mesh design of 5-7 mm are included in the analysis. Sample C is not provided with grooves. FIG. 8a shows the results after one segment, and it was very clear that Sample B has the best performance and Sample C the worst. The result after five segments had a completely different outcome, as shown in the FIG. 8b. Here Sample C had only improves slightly and still ended up with worst performance, whereas Sample A and Sample B improve were ending up with almost equally good performance.

Example 4

Testing Laser Cut Versus Knife-Cut

Figure 9A:
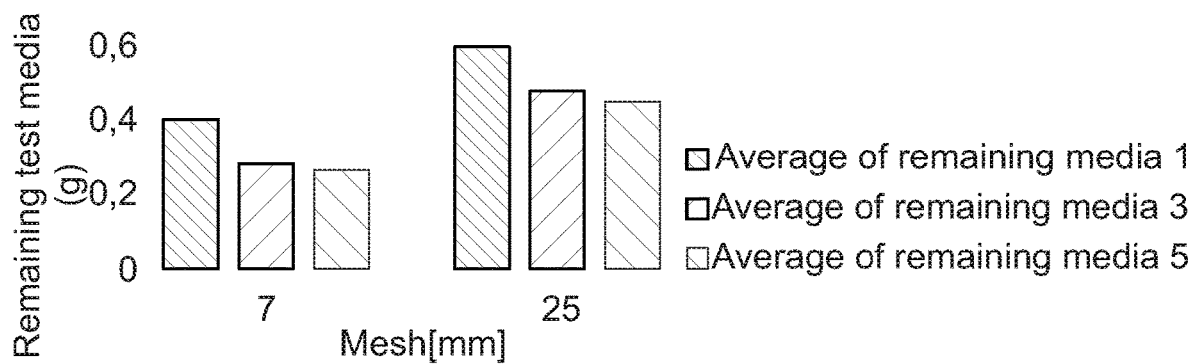
FIGS. 9a and 9b show the influence of different cutting methods.
Figure 9B:
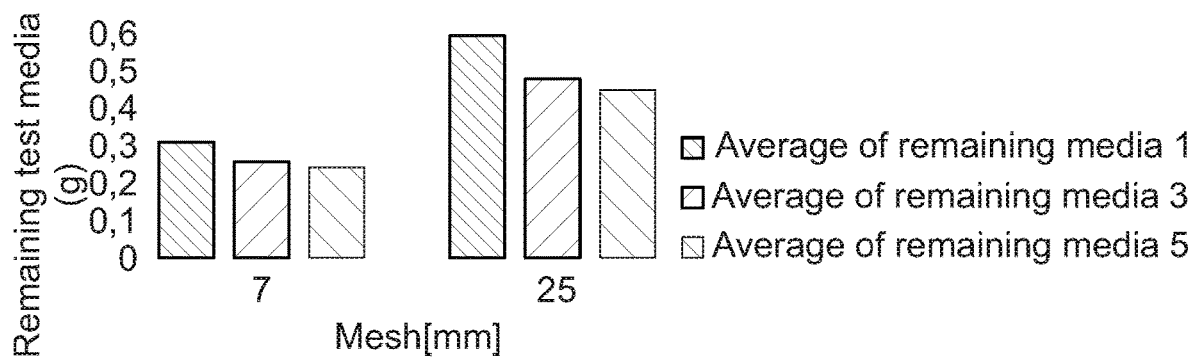

In FIGS. 9a and 9b is shown a comparison of laser cut samples (FIG. 9a) and knife-cut samples (FIG. 9b), mesh size 7 mm and sample without grooves (shown as 25 mm) and 10 g. initial test media with 48 Pa·s viscosity. The Samples used are Sample B. The first column represents results after 1 segment, the second column represents results after 3 segments and the third column represents results after 5 segments. No large significant effect is observed between the two ways of cutting the foam, both perform well.

Example 5

Testing of Slit Depth

Figure 10:
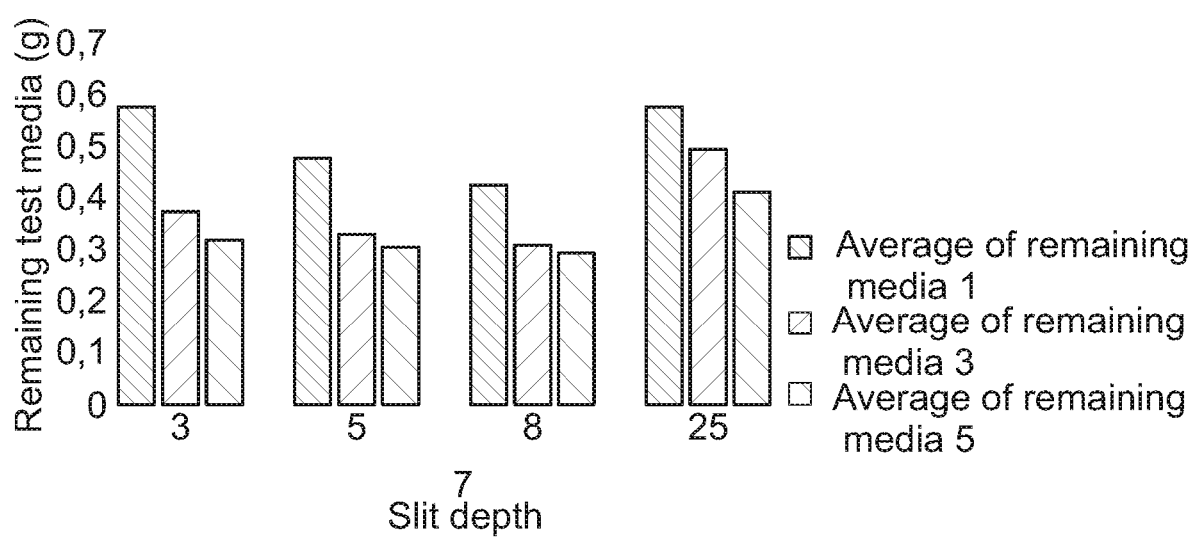
FIG. 10 illustrates the influence of different depths of the grooves.

In FIG. 10 is shown a bar diagram showing remaining test media as function as slit depth. All the samples (Sample A) have a slit size of 7 mm. The test was made on three different slit depths; 3, 5 and 8 mm and a sample without slits shown as 25 mm in the diagram). The different bars represent the data after 1, 3 and 5 segments, respectively. As can be seen from the Figure, the deeper slits, the better.

The invention claimed is:

1. A wound debridement device comprising:
a first foam layer coupled to a second foam layer that is different from the first foam layer;
wherein the first foam layer has a thickness measured from a first surface that is exposed to a second surface that is coupled to the second foam layer;
wherein the first surface includes a central portion and an edge portion surrounding an entirety of the central portion, where the central portion is provided with a plurality of grooves formed in the first surface, where each groove of the plurality of grooves extends into the first surface a groove distance that is less than the thickness of the first layer;
wherein the wound debridement device is adapted to clean a wound by capturing and retaining wound debris in the plurality of grooves by configuring:
the first foam layer to comprise pores in a range from 70-90 pores per inch with a Compression Load Deflection measured at 25% in a range between 0.30 to 0.40 psi, and
the second foam layer to comprise pores in a range from 40-50 pores per inch and a Compression Load Deflection measured at 25% in a range between 0.40 to 0.50 psi.

2. The wound debridement device of claim 1, wherein the plurality of grooves is oriented in a pattern of substantially parallel grooves.

3. The wound debridement device of claim 1, wherein the plurality of grooves includes a first set of grooves cut in one direction and a second set of grooves cut in a direction perpendicular to the first set of grooves.

4. The wound debridement device of claim 1, wherein the first foam layer is coupled to the second foam layer by an adhesive layer.

5. The wound debridement device of claim 1, wherein an outer perimeter of the device is substantially triangular.

6. The wound debridement device of claim 1, wherein the first foam layer has a first thickness and the second foam layer has a second thickness, and the first thickness is less than the second thickness.

7. The wound debridement device of claim 6, wherein a ratio between the first thickness and the second thickness is 1:2.

8. The wound debridement device of claim 1, wherein an outer perimeter of the device is substantially triangular formed by three sides, with an adjacent two sides of the three sides meeting at an apex, and the apex has rounded corners.

9. The wound debridement device of claim 1, wherein each of the plurality of grooves is separated from an adjacent groove by a ridge, where the ridge has an exposed ridge surface defined at the first surface of the first foam, and an angle measured from the exposed ridge surface to the adjacent groove is 90 degrees.

10. The wound debridement device of claim 1, wherein the first foam layer comprises a Compression Load Deflection measured at 65% in a range between 0.50 to 0.60 psi.

11. The wound debridement device of claim 1, wherein the plurality of grooves in the first surface of the first foam layer have a depth of at least 50% of a thickness of the first foam layer to configure the first foam layer to collect slough material from a wound.

12. The wound debridement device of claim 1, wherein the second foam layer comprises a Compression Load Deflection measured at 65% in a range between 0.65 to 0.75 psi.

13. The wound debridement device of claim 1, wherein the first foam layer is hydrophilic and the second foam layer is hydrophobic.

14. The wound debridement device of claim 1, wherein the edge portion is continuous and characterized by an absence of a groove.

15. The wound debridement device of claim 1, further comprising:
a reinforcing layer coupled between the first foam layer and the second foam layer.

16. The wound debridement device of claim 1, wherein a first groove of the plurality of grooves extends in a lateral direction across the central portion of the first surface and a second groove of the plurality of grooves extends in a longitudinal direction across the central portion of the first surface and cross through the first groove.

\* \* \* \* \*

UNITED STATES PATENT AND TRADEMARK OFFICE
CERTIFICATE OF CORRECTION

| | |
|---|---|
| PATENT NO. | : 11,452,639 B2 |
| APPLICATION NO. | : 16/648675 |
| DATED | : September 27, 2022 |
| INVENTOR(S) | : Igwebuike et al. |

It is certified that error appears in the above-identified patent and that said Letters Patent is hereby corrected as shown below:

In the Specification

In Column 7, Line 17, delete "first foam layer 30." and insert -- first foam layer 20. --, therefor.

Signed and Sealed this
Ninth Day of May, 2023

Katherine Kelly Vidal
*Director of the United States Patent and Trademark Office*